US006268211B1

(12) United States Patent
Jolicoeur

(10) Patent No.: US 6,268,211 B1
(45) Date of Patent: Jul. 31, 2001

(54) NON-INFECTIOUS HIV TRANSGENE

(75) Inventor: Paul Jolicoeur, Outremont (CA)

(73) Assignee: L'Institut de Recherches Cliniques de Montreal, Montreal (CA)

( * ) Notice: Subject to any disclaimer, the term of this patent is extended or adjusted under 35 U.S.C. 154(b) by 0 days.

(21) Appl. No.: 07/747,670

(22) Filed: Aug. 20, 1991

(51) Int. Cl.$^7$ .......................... C12N 15/63; C12N 15/09; C12N 15/00; C12N 5/00
(52) U.S. Cl. ................ 435/320.1; 435/455; 435/91.2; 435/69.1; 435/325; 536/27
(58) Field of Search .................. 536/27; 435/320.1, 435/172.3, 91, 69.1, 455, 91.2, 325; 935/23, 27

(56) References Cited

U.S. PATENT DOCUMENTS

| 4,736,866 | 4/1988 | Leder et al. ............................... 800/1 |
| 4,752,565 | * 6/1988 | Folks et al. ............................... 435/5 |

FOREIGN PATENT DOCUMENTS

| 91/02805 | 3/1991 | (WO) . |
| 91/05864 | 5/1991 | (WO) . |

OTHER PUBLICATIONS

E. Harlan and O. Prakash, Society for Neuroscience, Abstracts, vol. 16, 353 (1990), abstract 154.1.
J. Skowronski, J. Virol., 65 754 (1991).
Rekosh et al., Proc. Natl. Acad. Sci. 85: 334–338 (1988).*
Fisher et al., Nature 316: 262–265 (1985).*
Ratner et al., Nature 313: 277–284 (1985).*
Tremblay et al., Mol Cell. Biol. 9(2): 854–859 (1989).*
Southern et al., J. Mol. & Appl. Gen. 1: 327–341 (1982).*
L. Bouchard et al., Cell, 57, 931 (1989).
D. E. Mosier et al., Nature 335, 256 (1988).
J. M. McCune et al., Science, 241, 1632 (1988).
J.S. Khillan et al., Nucleic Acids Res., 16, 1423 (1988).
J. Vogel et al., Nature 335, 606 (1988).
J.M. Leonard et al., Science, 242, 1665 (1988).
J. Leonard et al., AIDS Res. Hum. Retroviruses, 5, 421 (1989).
P. Dickie et al., Sixth International Conference on AIDS, San Francisco, vols. 1–3, abstract Th. A. 290 (1990).
J. Dinchuk et al., Sixth International Conference on AIDS, San Francisco, vols. 1–3, abstract Th. A 291 (1990).

* cited by examiner

Primary Examiner—Jill D. Martin
(74) Attorney, Agent, or Firm—Foley & Lardner

(57) ABSTRACT

Disclosed herein is a transgenic non-human animal carrying a transgene which expresses non-infectious HIV ribonucleic acid and complementary proteins thereof. Among the expressed proteins, which can be found in the milk, serum and several tissues, are the gag and envelope proteins. The transgenic animal is useful as a source for obtaining the complementary proteins, and as an animal model to study HIV host cell interactions and to evaluate anti-HIV drugs.

6 Claims, 2 Drawing Sheets

NON-INFECTIOUS HIV TRANSGENE

FIELD OF INVENTION

This invention relates to a transgenic non-human mammal carrying a transgene which expresses a non-infectious human immunodeficiency virus ribonucleic acid (HIV RNA) and complementary proteins translated therefrom, to recombinant molecules containing the genetic sequence of the transgene, to a process for producing the transgenic mammal, and to methods of evaluating the pharmacokinetic effect of an agent on the expressed ribonucleic acid and/or proteins to determine the therapeutic value of the agent.

BACKGROUND OF THE INVENTION

In 1983, a retrovirus, known as human immunodeficiency virus type 1 (HIV-1), was established as a causitive agent of acquired immune deficiency syndrome (AIDS), see R. C. Gallo and L. Montagnier, Scientific American, 259 (4), 40 (1988). This virus has become a pestilence of alarming proportion. More recently, the closely related virus, human immunodeficiency virus type 2 (HIV-2) has been identified as a second causative agent of AIDS.

The identification of human immunodeficiency virus (HIV) as a causative agent and the development of methods to grow the virus in quantity have resulted in the discovery of compounds which inhibit the replication of HIV in vitro. The most important class of inhibitor compounds identified in this manner is a group of dideoxynucleosides of which 3'-azido-3'-deoxythymidine (known also as zidovudine or AZT) is used therapeutically to manage certain patients with symptomatic HIV infections. This class of compounds has been found to interfere with the life cycle of HIV by inhibiting reverse transcriptase. This enzyme converts viral RNA to double-stranded deoxyribonucleic acid (DNA) and as such is an essential enzyme for HIV replication. In addition to inhibiting reverse transcriptase, other stages of the HIV life cycle have been identified as targets for developing anti-AIDS drugs. One target that is receiving increased attention is an HIV-encoded enzyme known as HIV protease. This enzyme, like the reverse transcriptase, is encoded by the gag-pol gene and is essential for HIV growth. It is responsible for effecting certain cleavages within the gag (p55) or gag-pol (p180) protein precursors to release structural proteins and enzymes, including itself, found in mature infectious virions. Soon after infection, the protease may cleave the core nucleocapsid, thus triggering conformational changes of the ribonucleoprotein substrate and activating DNA synthesis. Thus, inhibitors of HIV protease may block several stages in the HIV life cycle. For a recent review on HIV-protease inhibitors, see B. M. Dunn and J. Kay, Antiviral Chemistry & Chemotherapy, 1, 3, (1990).

Notwithstanding the progress that has been made in the causes and treatment of AIDS, better small animal models are needed to study HIV infections and to evaluate potential drugs and vaccines. The need has resulted in the development of two small animal models based on severe combined immunodeficient (SCID) mice, D. E. Mosier et al., Nature, 335, 256 (1988) and J. M. McCune et al., Science, 241, 1632 (1988); These small animal models have the potential of being used for evaluating anti-AIDS drugs and vaccines. However, there is still a need for a small animal model to study HIV/host cell interactions and to screen for anti-HIV drugs.

The present invention offers to fulfil the latter need by providing a transgenic non-human mammal, for example a mouse or a rat, which expresses non-infectious HIV RNA, and the structural proteins, regulatory proteins and enzymes translated therefrom, and which can heritably transmit the transgene to its progeny.

The procedure for producing a transgenic animal is known in the art; for example, see B. Hogan et al., "Manipulating the Mouse Embryo: A Laboratory Manual", Cold Spring Harbor Laboratory, Cold Spring Harbor, N.Y., USA, 1986 and T. E. Wagner and P. C. Hoppe, U.S. Pat. No. 4,873,191, issued Oct. 10, 1989. However, the prior art also teaches that it is difficult, and not precisely understood how, to obtain an animal which carries a transgene functioning in a suitable physiological environment and in a desired manner, and which can produce offspring expressing the gene. The desired gene expression can be nullified if the cloned DNA is integrated into a region of the animal's chromosome that modifies its expression, or if it undergoes mutation or rearrangement in the process of being integrated into the chromosome; see, for example, H. Van der Putten et al., Mol. Gen. Genetic, 198, 128 (1984). Accordingly, a significant advance in the art of retrovirus transgenic animals, specifically HIV transgenic animals, can be realized by following the teaching of the present invention.

Previously reported production of transgenic animals include:

(a) & (b) transgenic mice containing human globin genes, T. A. Stewart et al., Science, 217, 1046 (1982) and E. F. Wagner et al., Proc. Natl. Acad. Sci. USA, 78, 5016 (1981);

(c) transgenic mice containing the human growth hormone gene fused to a metalothionein promoter sequence; R. D. Palmiter et al., Science, 222, 809 (1983);

(d) transgenic mice with a recombinant gene containing the rat elastase I promoter and the codons for human growth hormone, D. M. Ornitz et al., Nature, 313, 600 (1985);

(e) transgenic mice containing the human insulin gene, R. F. Selden and H. M. Howard, PCT patent application WO 87/07298, published Dec. 3, 1987;

(f) several transgenic mice cited in a review by G. Skangos and C. Bieberich, Advances in Genetics, 24, 285 (1987);

(g) several transgenic mice cited in a review by R. M. Strojek et al. entitled "The Use of Transgenic Animal Techniques for Livestock Improvement" in "Genetic Engineering: Principles and Methods", J. K. Setlow, Ed., Vol. 10, New York, N.Y., USA, 1988;

(h) transgenic non-human animals having a transgene with an activated oncogene sequence, P. Leder and T. A. Stewart, U.S. Pat. No. 4,736,866, issued Apr. 12, 1988;

(i) several transgenic animals cited in a review by J. Van Brunt, Bio/Technology, 6, 1149 (1988);

(j) transgenic animals, containing hormone encoded genes, from which hormones can be harvested, R. M. Evans et al., U.S. Pat. No. 4,870,009, issued Sep. 26, 1989;

(k) transgenic animals containing a gene capable of producing recombinant proteins in the animal's milk, H. Meade and N. Lonberg, U.S. Pat. No. 4,873,316, issued Oct. 10, 1989; and (l) transgenic mice, useful for analysis of hair growth, having recombinant genes comprising the regulatory elements involved in the expression of hair specific genes, A. R. McNab et al., Canadian patent application 2004156, published May 31, 1990.

Previous reports of transgenic mice carrying all or part of the HIV-1 genome include:

(a) a line of transgenic mice carrying only the long terminal repeat (LTR) of HIV fused to the chloramphenicol acetyl transferase (CAT) reporter gene, which were mated to transgenic mice of the opposite sex carrying the HIV-1 tat gene fused to a control element of the murine Aα crystallin gene to give progeny carrying both genes; hence, only a small portion of the HIV-1 genome is involved, J. S. Khillan et al., Nucleic Acids Res., 16, 1423 (1988);

(b) transgenic mice having the HIV-1 tat gene linked to the HIV-1 LTR in the absence of other parts of the HIV-1 genome and which developed skin lesions resembling Kaposi's sarcoma, J. Vogel et al., Nature, 335, 606 (1988);

(c) a single founder line of transgenic mice carrying a complete HIV-1 proviral genome wherein the offspring developed a disease syndrome resembling some aspects of the symptoms of AIDS patients, and marked by the presence of HIV in the tissues of the offspring and premature death thereof, J. M. Leonard et al., Science, 242, 1665 (1988);

(d) four lines of transgenic mice containing the HIV-1 LTR linked to the CAT reporter gene but no other parts of the HIV-1 genome and for which CAT activity was observed among mononuclear cells and maximally in Langerhans' cells, J. Leonard et al., AIDS Res. Hum. Retroviruses, 5, 421 (1989);

(e) trangenic progeny from three founder mice bearing chromosomally integrated copies of partial HIV-1 proviral DNA (rendered non-infectious by deletion of the gag-pol sequences) and which developed glomerulosclerosis, P. Dickie et al., Sixth International Conference on AIDS, San Francisco, Vols 1–3, abstract Th.A. 290 (1990);

(f) transgenic mice carrying HIV TAT and NEF genes under control of the HIV LTR, but no other parts of the HIV genome, as well as two transgenic founders carrying the HIV NEF gene construct (without TAT), J. Dinchuk et al., Sixth International Conference on AIDS, San Francisco, Vols. 1–3, abstract Th.A. 291 (1990);

(g) transgenic mice bearing the LTR of HIV (but no other parts of the HIV-1 genome) fused to the reporter gene CAT, one line of which showed CAT activity in the cerebellum, E. Harlan and O. Prakash, Society for Neuroscience, Abstracts, Vol. 16, 353 (1990), abstract 154.1; and (h) three lines of transgenic mice carrying a partial HIV genome comprising the HIV-1 LTR fused to the simian virus 40 early region, for which the transgene was observed in the lymphoid tissue and skin of the mice, J. Skowronski, J. Virol., 65, 754 (1991).

The transgenic animal of the present application is distinguished from the transgenic animals of the prior art in that it carries a non-infectious transgene having the complete coding sequence of the HIV genome, the transgene being capable of producing high levels of HIV proteins in several tissues and certain body fluids of the animal. The attainment of the present transgenic mammal is surprising indeed in view of previous reports that expression of HIV proteins was found to be very low in mouse fibroblasts transfected with the HIV genome; for example, see J. A. Levy et al., Science, 232, 998 (1986).

The term "HIV" as used includes both type 1 and type 2 human immunodeficiency viruses and their strains, unless it is used within the context of a specific embodiment related to type 1 or type 2 virus. The terms "HIV-1" and "HIV-2" are used to distinguish the type 1 virus and its strains from the type 2 virus and its strains. The HIV-1 and HIV-2 genomes, and the DNA sequences of HIV-1 and HIV-2, and respective strains are described in the publication, "Human Retrovirus And AIDS 1991",Eds. G. Myer et al., Theoretical Biology and Biophysics, Los Alamos National Laboratory, Los Almos, N. Mex., 87545, USA. The latter publication hereby is incorporated by reference.

SUMMARY OF THE INVENTION

The present invention provides a non-human transgenic mammal in which the germ cells and somatic cells carry a transgene capable of expressing non-infectious HIV ribonucleic acid (having the entire encoding sequence of the HIV genome) and complementary proteins in the cells. The transgene is introduced into the animal, or an ancestor of the animal, at an embryonic stage, preferably between the one-cell (or fertilized oocyte) and the 8-cell stage.

Among the expressed complementary proteins, which can be found in the milk, serum and several tissues of the transgenic animal are the gag protein (p55), the gag protein cleavage products p24 and p17, the envelope glycoprotein (gp160) and the envelope protein cleavage product gp120.

A noteworthy feature of the present transgenic animal is that it can produce progeny in which the gene is stably expressed. Hence, animal lines of the transgenic animal, having the same essential characteristics, are realized.

The transgene of the transgenic animal of this invention comprises (a) a non-infectious HIV proviral DNA sequence, (b) a surrogate promoter DNA sequence operatively linked to a tissue-specific DNA sequence to provide a surrogate promoter/tissue-specific enhancer, which in turn is operatively linked to the proviral DNA sequence, and (c) at least one polyadenylation addition signal DNA sequence operatively linked to the proviral DNA sequence.

A preferred embodiment of the transgene for use in the animal comprises (a) a proviral DNA sequence, coding for HIV-1 RNA, in which the 5'-long terminal repeat (5'-LTR) sequence, a portion of the 5' leader sequence and a portion of the 3'-long terminal repeat (3'-LTR) have been deleted, the deleted portions being predetermined to render non-infectious any HIV-1 RNA and complementary proteins expressed within the cells of the animal; (b) a surrogate promoter/tissue-specific enhancer DNA sequence operatively linked to the 5'-end of the proviral DNA sequence to drive the RNA expression of the transgene in a preselected tissue of the animal; and (c) one or more polyadenylation (poly A) addition signal sequences, operatively linked at the 3' end of the proviral DNA to provide 3' maturation and stabilization of the expressed RNA.

In a more preferred embodiment of the transgene, the surrogate promoter/tissue-specific enhancer sequence is the LTR promoter of the mouse mammary tumor virus (MMTV), also known as MMTV LTR, and the poly A addition signal sequence is the SV40 poly A addition signal.

Disclosed hereinafter are a process for preparing the aforementioned transgene from a recombinant DNA plasmid in which the DNA sequence of the transgene has been incorporated therein, and in turn a process for preparing the plasmid. The processes and the plasmid are included within the scope of this invention.

Also included within the scope of the invention is a method of producing a transgenic animal, carrying the aforementioned transgene, which can be stably bred to produce offspring containing the gene. The method comprises:

(a) isolating a fertilized oocyte from a first female animal;
(b) transferring the transgene into the fertilized oocyte;
(c) transferring the fertilized oocyte containing the transgene to the uterus of the same species as the first animal;
(d) maintaining the second female animal such that
   (i) the second female animal becomes pregnant with the embryo derived from the fertilized oocyte containing the transgene, (ii) the embryo develops into the transgenic animal, and (iii) the transgenic animal is viably born from the second female animal;

wherein the transgenic animal has the genetic sequence for non-infectious HIV proviral DNA and is capable of being bred to produce offspring having cells stably containing the genetic sequence.

Noteworthy is that by monitoring the effect of a test compound on the levels of expressed non-infectious RNA, and the translated proteins therefrom, e.g. the gag and envelope proteins and the gag protein cleavage products, the therapeutic value of a test compound for treating HIV infections in humans can be evaluated.

For instance, the proteins expressed in the cells of the transgenic animal include processed gag proteins resulting from the cleavage of the HIV-1 encoded gag-pol gene, the cleavage being effected by the HIV-1 encoded protease. Thus, the invention also provides a method for evaluating a test compound as a potential HIV-1 protease inhibitor. The method involves:

(a) administering the test compound to the transgenic animal, and (b) examining the effect or significance of the test compound on the expressed gag proteins in the animal by monitoring the expression levels of the proteins.

Likewise, since the presence of the gag and envelope proteins in the fluid and tissues of the transgenic animal denotes that the HIV regulatory protein, REV, is expressed, the present invention provides a method for evaluating a test compound as a potential inhibitor of REV function. The method involves:

(a) administering the test compound to the transgenic animal, and (b) examining the effect or significance of the test compound on the expressed gag and envelope proteins and the gag protein cleavage products in the animal by monitering the expression levels thereof.

Still another aspect of this invention involves the use of the transgenic animal for the production and isolation of the non-infectious RNA and its complementary proteins.

DETAILS OF THE INVENTION

Figure 1:
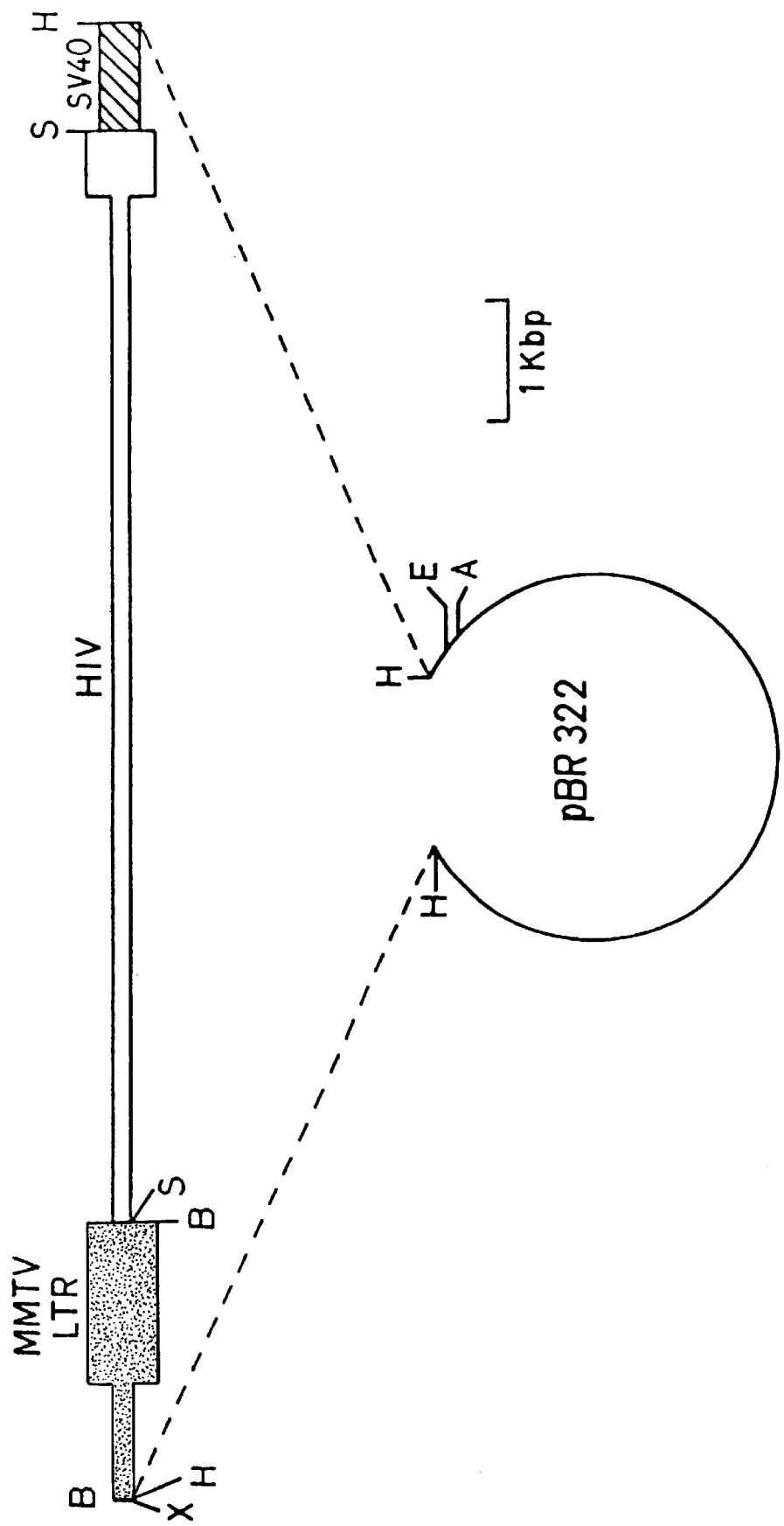
FIG. 1 is a diagrammatic representation of a region of a plasmid bearing the non-infectious HIV proviral DNA sequence and flanking regions. The restriction sites are A, AatII; B, BamH1; E, EcoR1; H, HindIII; S, SacI; and X, XbaI.

The term "gene" as used herein means the smallest, independently functioning DNA sequence which encodes for a protein product. An example of a gene is the DNA sequence which encodes for the gag protein.

The term "transgene" as used herein means exogenous genetic material which does not naturally form part of the genetic material of an animal to be genetically altered but can be incorporated into the germ and somatic cells of that animal by standard transgenic techniques. The transgene of the present invention is created by the serial ligation of a promoter DNA segment, a major portion of the HIV-1 genome including the coding region for gag-pol and envelope, and at least one poly A addition DNA sequence.

The term "operatively linked" as used herein in reference to units (i.e. distinguishable DNA sequences) of a transgene, means that the units to which the term is applied are linked according to recombinant technology techniques so that they may act together to control and express the transgene encoded RNA in a suitable tissue or cell type. An example would be the operatively linking of a promotor/tissue-specific enhancer to a DNA sequence coding for the desired proteins so as to permit and control expression of the DNA sequence and the production of the complementary proteins.

The term "promoter" as used herein means a DNA sequence which binds RNA polymerase and directs the enzyme to the correct transcriptional start site. The promoter is upstream of the HIV proviral DNA sequence to which it is operatively linked.

The term "enhancer" as used herein refers to a DNA sequence capable of increasing the transcription of the promoter. The term "promoter/tissue-specific enhancer" means a DNA sequence, having an activation site which is capable of being activated in a specific tissue or specific cell type, to promote the preferential transcription of a given gene to which the DNA sequence is operatively linked. Thus the transcription and expression of the transgene having the promoter/tissue-specific sequence will be enhanced within the specific tissue or cell-type. Examples of promoter/tissue-specific enhancers are the aforementioned MMTV LTR and the promoter/brain-specific enhancer, the myelin basic protein (MBP) promoter.

The term "complementary proteins" or "associated proteins" as used herein in relation to HIV-1 RNA refers to the initially translated proteins and their subsequent cleavage products. In particular, the term refers to the readily isolated and detectable proteins such as the HIV-1 gag protein (p55), the HIV-1 gag protein cleavage products p24 and p17, the envelope glycoprotein (gp160) and the envelope protein cleavage product gp120.

As indicated previously, procedures for producing transgenic animals have advanced considerably during the last ten years. This advance has provided new avenues for seeking improvement and creative applications. A compendium of the techniques can be found in the textbook by B. Hogan et al. entitled "Manipulating the Mouse Embryo: A Laboratory Manual", Cold Spring Harbor Laboratory, Cold Spring Harbor, N.Y., USA (1986). The latter reference is incorporated herein by reference.

More explicitly with regard to the present invention, the key feature is the realization of an animal carrying a transgene expressing non-infectious HIV RNA, which in turn is translated to give complementary HIV proteins in its body fluids and tissues.

Any mammal may be used in the production of the transgenic animal of this invention. The choice of animal will depend on the particular use planned for the transgenic animal.

When it is envisaged to use the transgenic animal as a model to study or evaluate the effects of a test compound on the expression of the HIV RNA and its complementary proteins, the practical choice of animal is one that is small, inexpensive and breeds readily and rapidly. In this case, the practical choice is a rodent, preferably a rat or a mouse. As noted in B. Hogan et al., supra, the mouse has been the favored small animal for the development and applications of transgenic technology; however the rat is also a practical animal species for this purpose; for example, see R. E. Hammer et al., Cell, 63, 1099 (1990).

When it is envisaged to use the transgenic animal as a source of HIV RNA and the complementary proteins thereof, i.e. for the production of research quantities of the non-infectious RNA transcript and associated proteins, e.g. gp160, gp120, p55, p41, p24, p17, REV, etc., a larger animal can be used. A convenient and practical process for such production purposes comprises the use of mammals that have long lactating periods and produce large volumes of milk; for example cows, sheeps, goats and pigs, which are genetically altered with a transgene of this invention so that the desired products are secreted into the mammal's milk. In this instance the transgene comprises a promoter/tissue-specific enhancer which is a mammary tissue specific promoter, or any promoter sequence known to be activated in mammary tissue, operatively linked to the non-infectious HIV proviral DNA sequence. The desired products are isolated from the collected milk of the animal by standard procedures.

The feasibility of using larger animals for the proceding production purposes is subscribed by previous reports of larger animals being successfully altered by transgenic technology; for example:

pigs, sheep and rabbits, R. E. Hammer et al., Nature, 315, 680 (1985), pigs and rabbits, G. Brem et al., Zuchthygiene, 20, 251 (1985), rabbits, K. Ross et al., Third FELASA Symposium, Amsterdam, Netherlands, Jun. 1–5, 1987;

sheep, C. Nancarrow et al., Theriogenology, 27, 263 (1987);

pigs, R. E. Hammer et al, Third International Symposium of Cellular Endrocrinology, Lake Placid, N.Y., USA, Aug. 30–Sep. 2, 1987, chicken, D. W. Salter et al., Virology, 157, 236 (1987), goats, J. D. Fabricant et al., Theriogenology, 27, 229 (1987), and sheep, J. P. Simons et al., Nature, 328, 530 (1987).

Hereinafter a preferred embodiment of this invention is disclosed in which the transgenic animal carries a transgene expressing HIV-1 RNA and the complementary proteins thereof. It should be noted, however, that the technology of the present application can be adapted to produce a transgenic animal carrying a transgene expressing HIV-2 RNA and the complementary proteins. Accordingly, either transgenic animal, whether expressing HIV-1 RNA or HIV-2 RNA, is considered to be within the scope of this invention.

More explicitly with regard to a preferred embodiment, the recombinant transgene comprises three fragments: firstly, a proviral DNA sequence having deleted portions at its 5' and 3' ends so as to render non-infectious the expressed HIV RNA and complementary proteins; secondly, a surrogate promoter/tissue-specific enhancer DNA sequence to drive the expression of the proviral DNA sequence; and thirdly, one or more poly A addition signal DNA sequences.

The promoter/tissue-specific enhancer is located upstream from the proviral DNA sequence; and the poly A addition signal sequence is located downstream of the proviral DNA sequence.

The HIV proviral DNA sequence is prepared by digesting a plasmid clone containing the DNA sequence of HIV-1 with a restriction enzyme that cleaves the HIV proviral DNA sequence at sites proximal to its 5' and 3' ends, removing essential controling sequences, to give a proviral DNA sequence truncated at both ends so that the eventual RNA expression from the cleaved fragment is rendered non-infectious, but still includes those elements required for the eventual production of the complementary proteins. In other words, the HIV genome lacks the sequences necessary for reverse transcription, integration and transcription. [The extent to which the 5' and 3' ends must be truncated to render the RNA non-infectious can be determined by standard methods; for example, by transforming the fragment so obtained into a genomic equivalent of HIV-1 and testing the resulting virus for cytopathic activity.] For example, a particular plasmid and restriction enzyme for effecting this result is the pBH10 plasmid [B. H. Hahn et al., Nature, 312, 166 (1984)] and the restriction enzyme SacI. The latter restriction enzyme cleaves the plasmid to give an HIV-1 genome deleted of its 5' LTR, part of its untranslated 5' leader sequence and a portion of its 3' end LTR.

One method, for example, for obtaining a non-infectious HIV proviral DNA sequence involves truncating the HIV genomic DNA fragment from its 5' end to a point on the untranslated 5' leader sequence located between about 50 nucleotides downstream from the 5' LTR and, but not including, the nucleotide marking the beginning of the splice donor sequence; and truncating the same HIV DNA fragment from its 3' end sequence to a point located downstream of the NEF gene, so that the complete encoding sequence of the NEF gene is retained and sequences required for virus replication (i.e. the U5, R and part of the U3 sequences) are deleted. (For the nucleotide sequence of HIV-1, HIV-2 and strains thereof, see "Human Retrovirus And AIDS 1991", supra).

Concerning the surrogate promoter/tissue-specific enhancers useful in various embodiments of this invention, any such promoter/enhancer which effectively drives the expression of the non-infectious HIV genome can be used. The choice of the promoter/enhancer depends on the tissue or tissues in which it is desired to express the HIV RNA and associated proteins. For instance, if it is desired to express the desired products in the milk, promoters which are known to be activated in the mammary gland are employed. Examples of such milk specific protein promoters are the casein promoters and the β-lactoglobin promoter, as well as the whey acidic protein (WAP) promoter. Among the promoters that are specifically activated in the milk and thus useful for expressing the desired products in milk according to the present invention is the MMTV LTR. By way of another example of promoters, when it is desired to specifically express the non-infectious RNA and associated proteins in the brain of the transgenic animal, promoters which are known to be activated in the brain are incorporated into the transgene. Such animals provide a useful in vivo model to evaluate the ability of a potential anti-HIV drug to cross the blood-brain barrier. Examples of brain-specific promoters are the myelin basic protein (MBP) promoter, the neurofilament protein promoter, the gonadotropin-releasing hormone promoter, the vasopression promoter and the neuron-specific enolase promoter, see S. Forss-Petter et al., Neuron, 5, 187, (1990). Other target cells for which specific promoters can be used are, for example, microphages, T cells and B cells. For a discussion of promoter/tissue-specific enhancers, see R. Jaenisch, Science, 240, 1468 (1988).

In a preferred embodiment of the transgene, the surrogate promoter/tissue-specific enhancer to drive expression of the HIV genome is the mouse mammary tumor virus long terminal repeat (MMTV LTR) sequence. This promoter is known to be tissue specific toward various epithelial and hemopoietic tissues, some of which naturally support lentivirus (and especially HIV) replication.

Concerning the poly A addition signal sequence, this fragment is one or a tandem of two to four of the known poly A addition signal sequences, such as those derived from the SV40 genome, the casein 3' untranslated region or other 3' untranslated sequences known in the art. A convenient and readily available source for the poly A addition signal is the commercially available pSV2neo vector from which the SV40 poly A addition signal sequence can be cleaved.

The transgene can be prepared from the aforementioned three fragment by using techniques known in the art; for example see J. Sambrook et al., "Molecular Cloning: A Laboratory Manual", 2nd ed, Vols 1 to 3, Cold Spring Harbor Laboratory Press, Cold Spring Harbor, N.Y., USA, 1989, herein incorporated by reference. More specifically, the three fragments can be ligated together with T4 DNA ligase in the presence of a restriction endonucleas-digested vector to produce the gene-carrying plasmid with the desired orientation of the fragments, i.e. so that they are operatively linked. Subsequent cleavage of the latter plasmid at appropriate unique sites is effected by restriction endonucleases to excise the linear transgene, which after appropriate purification is incorporated into the animal to be genetically altered.

The linear transgene (hereinafter sometimes referred to as the MMTV/HIV fragment) can be added to the gene pool of the animal to be altered by incorporating one or more copies of the transgene into the genome of a mammalian embryo by techniques known in the art. A practical technique is to introduce the transgene at the embryonic stage of the animal by microinjecting the transgene into a fertilized oocyte of the animal between the one-cell and eight-cell stage, preferably between the one-cell and four-cell stage. In this manner, between 5 to 30% of the animals developing from such oocytes contain at least one copy of the transgene in somatic and germ cells, and these founder animals transmit stably the transgene through the germ line to the next generation.

The biological profile of the present transgenic animal renders it useful as an animal model for studying HIV/host cell interactions and for evaluating potential anti-HIV agents acting at a post-integration step of the HIV life cycle. On the basis that the main structural gag proteins, e.g. p55, p41 and p24, are expressed in the animal cells, potential HIV-1 protease inhibitors can be evaluated since the HIV protease is essential for the processing of mature proteins from the gag-pol polyprotein. The presence of the RNA transcript and the presence or decrease (or disappearance) in the processed proteins in the cells serves as a means for evaluating HIV protease inhibitors.

On the basis that the main structural HIV proteins are properly made, especially the gag and envelope proteins and the gag cleavage products, potential REV function inhibitors can be evaluated since the REV function is essential for the production of those proteins. Thus, the monitoring of the levels of the latter proteins in the cells of the transgenic animal receiving a test agent provides a means for evaluating the anti-REV function activity of the agent.

Likewise, a potential inhibitor of cellular protease required for the processing of envelope glycoproteins, can be detected by monitoring the levels of gag and envelope proteins. In this instance, the cellular protease inhibitor does not affect the cellular levels of gag proteins but it does decrease the levels of the mature envelope glycoproteins, e.g. gp120, or cause their disappearance from the body cells. Thus, the comparative effects on the translation of gag and envelope proteins serves as an indication of cellular protease inhibition.

The following examples further illustrate this invention.

EXAMPLE 1

Construction of Transgene (12 kbp MMTV/HIV Fragment)

The transgene consisted of three fragments; the MMTV LTR promoter/tissue-specific enhancer sequence, the HIV proviral DNA sequence and the poly A addition signal sequence. The fragments were prepared as follows:

(a) MMTV LTR promoter sequence—The 2.3 (kbp) BamH1 MMTV fragment containing the 3' end sequences of the MMTV genome (including the 3' env sequences with the whole 3' end LTR) was obtained by digestion of plasmid pA9, A. L. Huang et al., Cell, 27, 245 (1981), followed by subcloning of the resulting fragment at the BamH1 site of plasmid pUC18 in an orientation which placed the end of the LTR close to the EcoR1 site. It was then prepared as a HindIII-SacI fragment by digestion with the restriction enzyme HindIII and then a partial digestion with the restriction enzyme SacI. Thus both of the enzymatic sites of the fragment were derived from the polylinker of the vector.

(b) HIV proviral DNA sequence—The 8.9 kbp SacI HIV-1 fragment was obtained by digesting the plasmid pBH10, B. H. Hahn et al., Nature, 312, 166 (1984), with SacI.

(c) poly A addition signal sequence—The SV40 poly A addition signal was prepared by cleaving the 885 bp BamH1—PstI fragment from the pSV2neo vector (ATCC 37149) and subcloning the fragment so obtained in the plasmid pUC18 (ATCC 37253). The SV40 fragment was then prepared from the subclone by digesting the subclone with SacI and HindIII.

Using T4DNA ligase, the three fragments from sections (a), (b) and (c) were ligated together in a HindIII-digested pBR322 vector in an orientation which placed the 3' end SV40 sequences close to the EcoR1 site of the plasmid pBR322. (See J. Sambrook et al., supra, section 1.12, for a description of pBR322.) In this manner, the gene-carrying pBR322 plasmid, incorporating the transgene DNA sequence (i.e. the 12 kbp MMTV/HIV fragment), was obtained. This plasmid is diagrammatically represented by FIG. 1.

The 12 kbp MMTV/HIV fragment for microinjection, see example 2, was obtained by cleaving the gene-carrying pBR322 plasmid with restriction enzymes XbaI and AatII. The fragment was isolated by agarose gel electrophoresis and further purified on CsCl gradients, essentially as described by B. Hogan et al., supra, p 159. In this manner, the 12 Kbp MMTV/HIV fragment was obtained wherein the proviral DNA sequence therein lacks the 5'-LTR sequence, a portion of the 5'-leader sequence and a portion of the 3'-LTR, thus rendering the fragment non-infectious.

EXAMPLE 2

Construction of Transgenic Mice

One-cell (C57BL/6×C3H)F2 embryos were collected, microinjected with the 12 Kbp MMTV/HIV fragment of example 1 (weight concentration=ca 1 $\mu$g/mL) and transferred into pseudopregnant CD-1 females essentially as described before [Hogan et al., supra and L. Bouchard et al., Cell, 57, 931 (1989)]. From 85 eggs, microinjected with the fragment and reimplanted, 17 mice were born, four of which were later found to be transgenic by Southern blot analysis of tail DNA with a $^{32}$P-HIV-1 specific probe (see J. Sambrook et al, supra, sections 9.31 to 9.57).

The HIV-specific probe was prepared by labeling the aforementioned 8.9 kbp SacI HIV-1 fragment with $^{32}$P-deoxycytosine triphosphate and deoxyadenosine triphosphate by the random primer method (see J. Sambrook et al., supra, section 10.13).

In each of the four transgenic mice, the MMTV/HIV sequences appeared intact and localized at an unique integration site (data not shown).

Three of the transgenic mice were bred successfully to C3H mice, obtained from Charles River Laboratories Canada Inc., St-Constant, Québec, Canada. These three founders transmitted the transgene to their progeny in a Mendelian fashion. The three lines, i.e. MMTV/HIV-R3, MMTV/HIV-R4 and MMTV/HIV-R10, were thus established by mating founder mice to C3H mice.

EXAMPLE 3

Transgenic Mouse Studies (a) Phenotype of Mice Carrying the MMTV/HIV Transgene

No phenotype was apparent in the transgenic mice. They looked, behaved and moved like the age-matched, non-transgenic mice. At autopsy, macroscopic examination of the transgenic mice indicated that they were normal.

(b) RNA Transcript

HIV-1 RNA expression of the transgene was detected by the agarose gel transfer (Northern) procedure, using total RNA from various organs of representative transgenic mice.

More particularly, the total RNA was isolated by the method of P. Chomczynski and N. Sacchi, Anal. Biochem., 162, 156 (1987) and analyzed by the Northern blot procedure (see J. Sambrook et al., supra, section 7.39). RNA was separated on 1% formaldehyde-agarose gels, transferred to nylon membranes (Hybond-N®, Amersham Canada Ltd., Oakville, Ontario, Canada) and hybridized with the aforementioned $^{32}$P-HIV-specific probe according to the method of L. Singer and K. W. Jones, Nucl. Acids Res., 12, 5627 (1984).

The three main species of HIV-1 RNA (classified according to their molecular weight), usually detected in cells productively infected with HIV-1, were detected in several organs known to support transcription from the MMTV LTR, such as mammary, Harderian and salivary glands, epididymis, thymus and spleen, in the three transgenic lines tested. Additional investigations were carried out on other organs of the mice of the line MMTV/HIV-R10. In those organs which are known to support MMTV-LTR-driven transcription poorly, such as the kidney, liver or brain, the examination of the organs for transgene RNA transcript indicated that the transgene was not expressed, as expected.

(c) Expression of HIV Structural Proteins in Organs of the Transgenic Mice

To determine whether the HIV-1 RNA found in organs of the transgenic mice was translated, the levels of HIV structural proteins in these organs were measured by the Western blotting procedure (see E. Harlow and D. Lane, "Antibodies: A Laboratory Manual", Cold Springs Harbor Laboratory, Cold Springs Harbor, N.Y., USA, 1988, section 12) with antisera specific to HIV-1 proteins. The env gp160 and gp120 were detected at very high or moderate levels in the mammary glands of animals of three transgenic lines, at lower levels in the salivary and Harderian glands, and in the liver, seminal vesicles, epididymis and testis of mice from the line MMTV/HIV-R10, and in the epididymis, spleens or livers of mice from line MMTV/HIV-R4. These proteins comigrated with authentic HIV env proteins from HIV-1 infected cells, except that the transgenic gp120 migrated slightly faster.

The gag p55 precursor protein was detected at high levels in mammary glands of animals of the three transgenic lines. The p55 and/or p41 proteins were detected in the salivary and Harderian glands, and in the spleen, seminal vesicles and epididymis of mice from line M/HIV-R10 and in the spleen and epididymis of mice from line MMTV/HIV-R4. The mature cleavage product, the p24 gag protein was detected in mammary glands of mice from line MMTV/HIV-R10 and MMTV/HIV-R3 and in the salivary glands of animals from line MMTV/HIV-R10. The p55, p41 and p24 proteins from the above designated organs of the transgenic mice migrated with corresponding authentic proteins from HIV-1 infected human T-cells, indicating proper synthesis and cleavage in these mouse organs.

In serum, HIV-1 proteins reactive with HIV-specific antibodies were detected in mice from two lines (MMTV/HIV-R4 and MMTV/HIV-R10). Higher levels of HIV-1 serum proteins were detected in lactating female mice.

Figure 2:
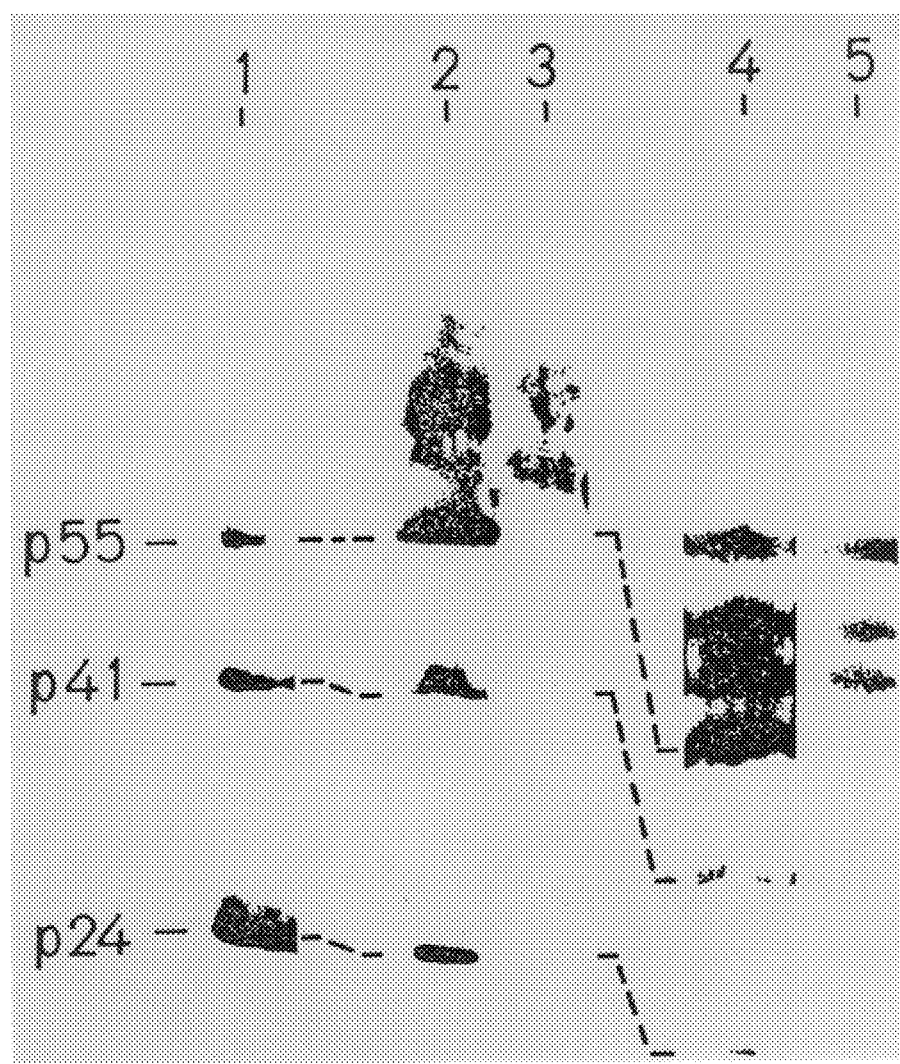
FIG. 2 is a reproduction of a photograph of a Western blot analysis of human T-cells infected with HIV-1 (lane 1), milk from representative female transgenic mice of this invention (lanes 2 and 4) and milk from normal C3H mice (lanes 3 and 5). The HIV gag proteins are similarly processed in human T-cells and in the transgenic mouse. No HIV-specific proteins are detected in the milk of the normal mouse.

The HIV env (gp 160 and gp 120) and gag (p55, p41 and p24) proteins were also detected at very high levels in milk from lactating female transgenic mice (see FIG. 2). In addition, HIV proteins were detected at a lower level in the secretions of the male genital tract. These results were expected since the mammary glands as well as the epididymis were positive for HIV-1 proteins, see above.

These results clearly indicated that several mouse specialized cell types are capable of releasing HIV proteins extracellularly either in the circulation or in secretions.

Search for the Presence of MuLV(HIV) Pseudotypes in Serum of Transgenic Mice

HIV and murine leukemia viruses (MuLV) have been shown to form pseudotypes under certain experimental conditions. Although a short leader sequence necessary for HIV RNA packaging is still present in the transgene, the HIV RNA sequences transcribed in these mice would not be expected to be packaged very efficiently, due to the absence of other leader and LTR sequences. Moreover, if packaged, these sequences would not be expected to be reverse transcribed, because of the absence of U5, R and part of the U3 sequences of HIV-1. HIV proteins, however, should be able to form pseudotypes with MuLV proteins and may be able to package endogenous MuLV RNA.

To detect infectious particles having a MuLV RNA genome and HIV env proteins, A3.01 cells, known to be resistant to ecotropic and xenotropic MuLV infection but sensitive to MuLV replication and harboring the CD4 receptor for HIV, were used. These human cells, possibly infected and producing MuLV, were cocultivated with NIH/3T3 or mink cells, respectively susceptible to ecotropic or xenotropic MuLV. No such MuLV (HIV) ecotropic or xenotropic pseudotype was detected in serum of the transgenic mice from lines MMTV/HIV-R4 and MMTV/HIV-R10 indicating that these pseudotypes were absent or below the sensitivity of the assay.

Therefore, it appears that the formation of MuLV (HIV) pseudotypes is not characteristic of these transgenic mice.

In conclusion, the transgenic animal of the invention therefore provides a safe and practical model to study the effects of test compounds, when administered systemically to the animal, on the expressed HIV RNA, processed gag proteins, the pol encoded enzymes, envelope proteins and regulatory proteins (e.g. REV). For instance, the readily measurable high levels of the HIV-1 gag reactive proteins, p55, p41 and p24, in the milk of the lactating female transgenic mice, noted above, renders the latter animal a convincing and practical model for evaluating a test compound as a HIV-1 protease inhibitor by administering the test compound, po, sc, ip or iv, to the animal, and monitoring the effect of the test compound on the expression levels of the HIV-1 gag reactive proteins in the milk of the animal, for example, by the Western blotting procedure utilizing a gag p24 or p17 specific antibodies.

Furthermore, it will be apparent to the practitioner of transgenic animal technology that the advantages of the present invention accrue from the inactivation of infectivityconferring regions of the LTR's and immediate flanking regions of HIV genome to obtain a transgene capable of expressing non-infectious HIV RNA. Hence, without further elaboration, the present disclosure allows the practitioner to ascertain the extent to which the invention can be utilized, and to appreciate that variations in the extent and location of deletion or the substitution of nucleotide residues of the LTR's or their immediate flanking regions to render the expressed HIV RNA of a transgene non-infections would be encompassed by the present invention.

I claim:

1. A recombinant transgene which comprises:
   (a) a HIV DNA which is a complete HIV genome except in having deleted therefrom the 5'-LTR, a portion of the 5' leader and a portion but not all of the 3'-LTR, wherein said HIV DNA encodes a substantially complete HIV RNA and said deletions render non-infectious said HIV DNA and RNA and the complementary proteins expressed from said DNA or RNA;
   (b) a surrogate promoter and surrogate tissue-specific enhancer operatively linked to said HIV DNA; and
   (c) a polyadenylation signal operatively linked to said HIV DNA.

2. The recombinant transgene as recited in claim 1 wherein the proviral DNA sequence is a HIV-1 RNA encoding DNA sequence.

3. The recombinant transgene as recited in claim 1, wherein said HIV DNA is a HIV-1 RNA encoding HIV DNA, said surrogate promoter/tissue-specific-enhancer is the MMTV LTR promoter and said poly A addition signal sequence is the SV40 poly A addition signal.

4. A process for preparing a DNA for expression of a non-infectious, substantially complete HIV RNA, wherein said DNA comprises a complete HIV genome except in having deleted therefrom the 5'-LTR, a portion of the 5' leader and a portion of the 3'-LTR, said process comprising:
   (a) providing in a first DNA fragment a non-infectious HIV DNA which is a complete HIV genome except in having deleted therefrom the 5'-LTR sequence, a portion of the 5' leader sequence and a portion but not all of the 3'-LTR;
   (b) operably linking to the 5' end of said HIV genome a surrogate promoter and a surrogate tissue-specific enhancer comprised in a second DNA fragment;
   (c) operably linking to the 3' and of said HIV genome a polyadenylation signal comprised in a third DNA fragment; and
   (d) ligating said operably linked fragments of (a), (b) and (c) into a vector for expression of said non-infectious HIV genome in a cell.

5. A process according to claim 4 wherein said vector is prepared for ligation by digestion with a restriction endonuclease.

6. A process according to claim 4, wherein said vector is the plasmid pBR322 digested with HindIII.

* * * * *